(12) United States Patent
Lai et al.

(10) Patent No.: US 11,499,966 B2
(45) Date of Patent: Nov. 15, 2022

(54) ENCODED MICROFLAKES

(71) Applicant: WinMEMS Technologies Co., Ltd., Taoyuan (TW)

(72) Inventors: Chih-Hsiang Lai, Taipei (TW); Wen-Ching Lai, New Taipei (TW)

(73) Assignee: WinMEMS Technologies Co., Ltd., Taoyuan (TW)

( * ) Notice: Subject to any disclaimer, the term of this patent is extended or adjusted under 35 U.S.C. 154(b) by 0 days.

(21) Appl. No.: 17/743,415

(22) Filed: May 12, 2022

(65) Prior Publication Data

US 2022/0276236 A1    Sep. 1, 2022

Related U.S. Application Data

(62) Division of application No. 16/601,982, filed on Oct. 15, 2019, now Pat. No. 11,366,109.

(60) Provisional application No. 62/776,224, filed on Dec. 6, 2018.

(51) Int. Cl.
*G01N 33/543* (2006.01)

(52) U.S. Cl.
CPC .............. *G01N 33/54326* (2013.01)

(58) Field of Classification Search
None
See application file for complete search history.

(56) References Cited

U.S. PATENT DOCUMENTS 3,405,578 A * 10/1968 Persson .................. G01B 11/26
356/138

* cited by examiner

*Primary Examiner* — Elizabeth A Robinson
*Assistant Examiner* — Ryan J Dowty
(74) *Attorney, Agent, or Firm* — Tong J. Lee

(57) ABSTRACT

A digitally encoded microflake includes a polymer layer, which has a top surface and a bottom surface substantially parallel to the top surface. At least one of the top surface and the bottom surface is to be coupled to target-specific probes for bonding with a target analyte. The microflake is identified by a binary sequence of bits encoded by an edge outline on a plane substantially parallel to the top surface and the bottom surface. The bits in the binary sequence are encoded at respective predefined locations surrounding the edge outline.

12 Claims, 14 Drawing Sheets

Code= 01100110000011001101110001100000011000
MSB ← — — — — — — — — — — — — — — — — LSB Code= 01100110000011001100000000011000000011000
MSB ← — — — — — — — — — — — — — — — — LSB Code= 110000001101100000110000110000011001100
MSB ← — — — — — — — — — — — — — — — — LSB Code = 00000111100001100001100000
MSB ← LSB Code=111111111111111111111111111111

Code=000000000000000000000000000000

Code=101010101010101010101010101010
MSB ← LSB

Code=010101010101010101010101010101
MSB ← LSB

ENCODED MICROFLAKES

CROSS-REFERENCE TO RELATED APPLICATIONS

This application is a divisional application of U.S. patent application Ser. No. 16/601,982 filed on Oct. 15, 2019, which claims the benefit of U.S. Provisional Application No. 62/776,224 filed on Dec. 6, 2018, the entirety of which is incorporated by reference herein.

TECHNICAL FIELD

Embodiments of the invention relate to microflakes encoded with digital codes and the fabrication process of the microflakes.

BACKGROUND

With the development of precision medicine, personalized medicine, and preventive medicine, there is a need in the field of in-vitro diagnosis (IVD) for performing assays on a large number of targets in biological test samples. A multiplex approach, known as multiplex assays, enables multiple measurements to be simultaneously performed on multiple different targets to increase test throughput and reduce cost. Multiplex assays have a wide range of applications such as pathological diagnosis (e.g., infectious disease or oncology), food safety, human and animal disease control, environmental monitoring, biomedical science research, drug screening and discovery, etc.

To conduct a multiplex assay, reagents such as probes are immobilized on the solid-phase surface of microcarriers. Depending on the type of the desired target, the probe can be an antibody, a protein, an antigen, a DNA, an RNA or another molecule with an affinity for the desired target. Microcarriers with different probes are added into a test sample, such that the probes and the corresponding targets in the test sample make specific bonding. Excess substances not bounded to any probes may be washed and removed. Detection antibodies or other suitable agents can be added to the targets to form specific bonding. These detection antibodies or suitable agents may contain a fluorophore, which emits light upon excitation by a tight source. The emitted light allows those targets that are bounded to the probes to be observed and quantified.

A test sample in a multiplex assay typically contains multiple targets of interest. To keep track of which targets are bounded to the probes on the microcarriers, various approaches have been developed to encode microcarriers, such that microcarriers with different probes can be distinguished from one another.

For example, one approach is to label different microcarriers with different fluorescent dyes; however, the number of available fluorescent dyes is typically insufficient for multiplex assays where high throughput is desired. Another approach is to encode a microcarrier with a pattern of opaque segments and transparent gaps, where the pattern is enclosed within the microcarrier.

Conventional approaches such as the ones described above generally have several disadvantages such as high fabrication cost, insufficient reaction surface, poor performance, etc. Thus, there is a need for improving the design and fabrication of encoded microcarriers.

SUMMARY

In one embodiment, a microflake is provided. The microflake includes a polymer layer, which has a top surface and a bottom surface substantially parallel to the top surface. At least one of the top surface and the bottom surface is to be coupled to target-specific probes for bonding with a target analyte. The microflake is identified by a binary sequence of bits encoded by an edge outline on a plane substantially parallel to the top surface and the bottom surface. The bits in the binary sequence are encoded at respective predefined locations surrounding the edge outline.

In another embodiment, an apparatus for a multiplex assay is provided. The apparatus comprises a first microflake to form a target-specific bonding to a first target analyte, and a second microflake to form a target-specific bonding to a second target analyte which is different from the first target analyte. The first microflake is identified by a first binary sequence, and the second microflake is identified by a second binary sequence different from the first binary sequence. The first binary sequence is encoded by a first edge outline on a first plane substantially parallel to a top surface and a bottom surface of the first microflake, and bits in the first binary sequence are encoded at respective predefined locations surrounding the first edge outline. The second binary sequence is encoded by a second edge outline on a second plane substantially parallel to a top surface and a bottom surface of the second microflake, and bits in the second binary sequence are encoded at respective predefined locations surrounding the second edge outline.

In yet another embodiment, a semiconductor wafer is provided. The semiconductor wafer comprises a substrate; a plurality of first microflakes on the substrate; and a plurality of second microflakes on the substrate. Each first microflake is identified by a first binary sequence, and each second microflake is identified by a second binary sequence different from the first binary sequence. Each first microflake is identified by a first binary sequence encoded by a first edge outline on a plane substantially parallel to the substrate, and bits in the first binary sequence are encoded at respective predefined locations surrounding the first edge outline. Each second microflake is identified by a second binary sequence encoded by a second edge outline on the plane, and bits in the second binary sequence are encoded at respective predefined locations surrounding the second edge outline.

Other aspects and features will become apparent to those ordinarily skilled in the art upon review of the following description of specific embodiments in conjunction with the accompanying figures.

BRIEF DESCRIPTION OF THE DRAWINGS

The present invention is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one. Further, when a particular feature, structure, or characteristic is described in connection with an embodiment, it is submitted that it is within the knowledge of one skilled in the art to effect such feature, structure, or characteristic in connection with other embodiments whether or not explicitly described.

DETAILED DESCRIPTION

Figure 1A:
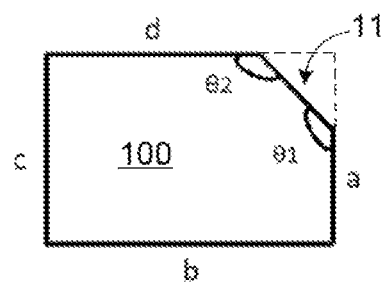
FIGS. 1A and 1B illustrate two opposite surfaces of a microflake according to one embodiment.

In the following description, numerous specific details are set forth. However, it is understood that embodiments of the invention may be practiced without these specific details. In other instances, well-known circuits, structures and techniques have not been shown in detail in order not to obscure the understanding of this description. It will be appreciated, however, by one skilled in the art, that the invention may be practiced without such specific details. Those of ordinary skill in the art, with the included descriptions, will be able to implement appropriate functionality without undue experimentation.

Described herein are microflakes which may be used as carriers for analyte detection and analysis in multiplex assays. Microflakes, also referred to as digital magnetic flakes in some embodiments, can be identified by their respective digital identifiers (also referred to as digital code, or code). In one embodiment, the digital identifier of a microflake is encoded by a sequence of notches and edge segments at the periphery (i.e., edge) of the microflake. By detecting an edge outline of a microflake, a detector can identify the code associated with the microflake. More specifically, the edge outline, which outlines the periphery of the microflake on a plane substantially parallel to the top surface and the bottom surface of the microflake, encodes a binary sequence identifying the microflake.

When used in a multiplex assay, microflakes having the same code are coupled to the same type of probe for capturing the same target analyte, and microflakes having different codes are coupled to different types of probes for capturing different target analytes.

In one embodiment, microflakes may include a magnetically responsive material to facilitate handling and collection. The magnetically responsive material may constitute substantially all of a microflake, a portion of a microflake, or only one component of a microflake. The remainder of the microflake may include, among other things, polymeric material, coatings, and moieties which permit attachment of a probe. Examples of the magnetically responsive material include magnetic metals such as iron, nickel, cobalt, and alloys of rare-earth metals, but are not limited thereto. In one embodiment, a magnetic metal strip may be embedded within a non-magnetic polymer layer of the microflake. The non-magnetic polymer layer may be substantially transparent. Alternatively, a microflake may be made of a magnetic photoresist material; e.g., a mixture of magnetic particles and polymer. The magnetic photoresist material may be substantially transparent. However, it is noted that the microflake may be made of materials different from the aforementioned materials.

A microflake may have any degrees of transparency. In one embodiment, a microflake is substantially transparent. In another embodiment, a microflake is at least partially transparent. As used herein, a material is "substantially transparent" means that a high percentage of light can pass through the material (e.g., over 50% of light). A material is "partially transparent" when it is less transparent than a substantially transparent material and more transparent than an opaque material.

Microflakes may be fabricated using a wide variety of materials; for example, resins and polymers. Examples of polymers include polystyrene, polydivinylbenzene, polymethylmethacrylate, poly-lactides, polyclycolides, polycaprolacton and copolymers thereof. Alternative materials may also be used. In some embodiments described herein, the body of a microflake is made of a substantially transparent polymer material. A microflake can be of any color.

In one embodiment, the digital codes of the microflakes described herein are formed by a substantially transparent polymer material. When used in a multiplex assay, the microflakes that bond with fluorophore-labeled target analytes emit fluorescent light upon excitation by a light source (e.g., an ultraviolet light source). The light excitation may be performed once and the resulting microflake images (which are illuminated by fluorescence) can be used for identifying their respective codes as well as for the analysis (e.g., quantification) of the target analytes. The edge outlines of these fluorescence-illuminated microflake images can be easily detected against a dark background. Those microflakes that do not emit fluorescent light upon excitation do not bond with any target analytes, and, therefore, do not need to be decoded.

By contrast, a conventional microcarrier encoded with an embedded opaque material may need two steps of light excitations. In the first step, all of the microcarriers in a sample are illuminated by a first light source in a first light spectrum (e.g., ultraviolet light) for the purpose of analyzing (e.g., quantifying) the target analytes. In the second step, all of the microcarriers in the sample are again illuminated by a second light source in a second light spectrum (e.g., visible light) for the purpose of identifying their codes. In the first step those microcarriers bonded with target analytes are fluorescence-illuminated against a dark background; however, the code patterns formed by the embedded opaque material typically cannot be decoded under the fluorescence. One reason is that the fluorescence is emitted from the microcarrier surface, which does not provide sufficient illumination for distinguishing embedded opaque code patterns. Therefore, the second step is generally needed by the conventional designs to illuminate the microcarriers in visible light. The additional step (i.e., the second step) increases the complexity of the decoding process.

Furthermore, in a multiplex assay where a microflake has probes on both the top and bottom surfaces, all of these probes can capture a fluorophore-labeled target analyte and the microflake can be illuminated on both surfaces by the fluorescence. Higher transparency of the microflake means that not only the fluorescence from the top (front) surface can be detected, but also the fluorescence from the bottom (back) surface can pass through the microflake body and be detected. Thus, a detector may read the code identifying the microflake more easily from the image of the fluorescence-illuminated microflake. However, it is understood that the microflake encoding schemes described herein are applicable to microflakes of any degree of transparency.

A microflake is a substantially flat microcarrier with substantially planar top and bottom surfaces. The size of a microflake, when measured from the longest dimension (e.g., the diameter or the diagonal length at the top or bottom surface) is typically in the range of a few μm to hundreds μm. The thickness of a microflake is typically in the range of 1 μm to 10 μm.

In one embodiment, a microflake is encoded by one or more types of notches at its edge. A first-type notch is an orientation indicator that identifies an orientation of the microflake; e.g., the top surface or the bottom surface. The first-type notch further indicates a starting point of a binary sequence and a direction along which the binary sequence is to be read, where the binary sequence is the code identifying the microflake. A second-type notch is used for encoding the microflake. In one embodiment, a microflake is encoded by its edge outline which includes a sequence of edge segments and second-type notches. The sequence of edge segments and second-type notches encodes the binary sequence of zeros and ones.

The first-type and the second-type notches may have V-shape, U-shape, square-shape, rectangular shape or the like, at the edge of the microflake. In some embodiments, a first-type notch may be formed by removing a corner of a polygon. Each of the notches (including the first-type notches and the second-type notches) extends from the top surface to the bottom surface of the microflake.

In the following description, the term "substantially parallel" is used herein to mean that two lines, layers or planes are parallel or may be deviated slightly from being parallel. The slight deviation may come from the fabrication process and is within an allowable tolerance range. Thus, the terms "parallel" and "substantially parallel" are interchangeable in this disclosure to mean that two or more lines, layers, and/or planes are parallel within an allowable tolerance range. Similarly, the terms "substantially planar," "substantially vertical" and "substantially perpendicular" are used to indicate "planar," "vertical" and 'perpendicular," respectively, within an allowable tolerance range.

Figure 1B:
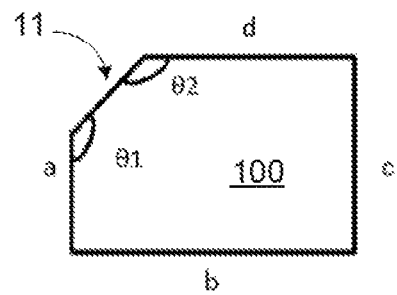
Figure 2A:
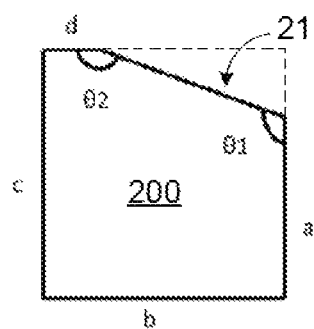
FIGS. 2A and 2B illustrate two opposite surfaces of a microflake according to another embodiment.
Figure 2B:
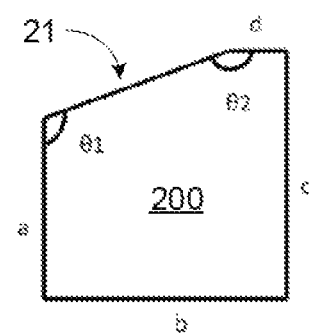
Figure 3A:
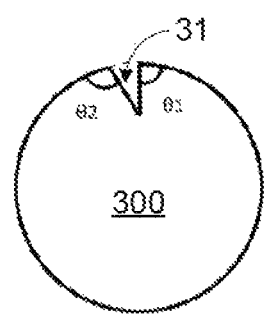
FIGS. 3A and 3B illustrate two opposite surfaces of a microflake according to yet another embodiment.
Figure 3B:
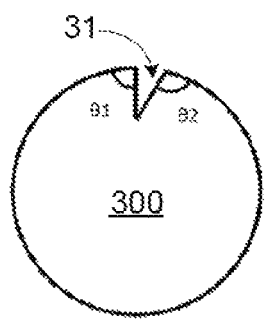

FIGS. 1A, 1B, 2A, 2B, 3A and 3B are schematic diagrams illustrating microflakes 100, 200 and 300 according to some embodiments. Each of the microflakes 100, 200 and 300 has only the first-type notch (11, 21, and 31, respectively) present at the edge. FIGS. 1A, 2A and 3A illustrate the top surfaces of the microflakes 100, 200 and 300, respectively, and FIGS. 1B, 2B and 3B illustrate the bottom surfaces of the microflakes 100, 200 and 300, respectively.

It is noted that the terms "top" and "bottom" are used herein to name the two opposite surfaces of a microflake. In use (e.g., during a multiplex assay process), the bottom surface may be on top while the top surface may be on the bottom of a microflake, or vice versa.

The examples herein illustrate that a microflake can be of any shape as its base shape; e.g., a polygon, a circle, or the like. It is noted that the base shape of a microflake refers to the shape of a microflake without any of the notches.

The first-type notches 11, 21, and 31 define the orientation (e.g., front or back, top or bottom) of the respective microflakes 100, 200 and 300. A detector can identify whether an observed surface of a microflake is the top surface or the bottom surface of the microflake; e.g., by identifying the lengths of the two adjacent sides or the two adjacent angles of the first-type notch. After the detector identifies which surface of the microflake is being or has been observed, the detector or another device can then determine the direction in which the code at the edge of the microflake is to be read.

FIG. 1A further shows that the first-type notch 11 may be formed by removing a triangular portion of a corner (shown in dotted lines). The part of the edge outline that defines the first-type notch 11 may be a straight line (which is shown in FIG. 1A), a curved line, or another shaped line. As shown in FIG. 1A and FIG. 1B, the first-type notch 11 forms an asymmetric relationship with its two adjacent sides (e.g., "a" and "d"), where a and d have different lengths (e.g., a<d). This difference in adjacent side lengths helps a detector to determine whether an observed surface of a microflake is the top surface or the bottom surface of the microflake. For instance, an identifier may be encoded in the form of a sequence of second-type notches and/or edge segments of a microflake. The sequence read clockwise from the top surface of the microflake can be different from the sequence read clockwise from the bottom surface of the microflake. To correctly read and interpret a detected sequence, the detector first uses the first-type notch to identify the surface of the microflake. In the example of FIGS. 1A and 1B, the detector may identify whether the observed surface is the top surface or bottom surface by reading the side lengths clockwise from the first-type notch. That is, if the lengths are read as a→b→c→d, then the observed surface is the top surface. However, if the lengths are read as d→c→b→a, then the observed surface is the bottom surface. In one embodiment, the detector may compare the lengths of the first-type notch's two adjacent sides by following a predetermined direction (e.g., clockwise) to determine which surface of the microflake is being or has been observed. When read in the clockwise direction, if the first-encountered adjacent side (e.g., a) is shorter than the second-encountered adjacent side (e.g., d), then according to the example of FIG. 1A, the observed surface is the top surface. Similarly, when read in the clockwise direction, if the first-encountered adjacent side (e.g., d) is longer than the second-encountered adjacent side (e.g., a), then according to the example of FIG. 1B, the observed surface is the bottom surface.

Alternatively or additionally, the first-type notch 11 may form an asymmetric relationship with its two adjacent angles (e.g., $\theta_1$ and $\theta_2$), where $\theta_1$ and $\theta_2$ have different values (e.g., $\theta_1 > \theta_2$). Each adjacent angle is defined by a side of the first-type notch 11 and one adjacent side of the microflake 100. This difference in the adjacent angles helps a detector to determine whether an observed surface of a microflake is the top surface or the bottom surface of the microflake. For instance, the detector may determine the observed surface to be the top surface if the first-encountered angle read clockwise from the first-type notch 11 is Oi, or if the two adjacent angles read clockwise from the first-type notch 11 is $\theta_1 \rightarrow \theta_2$, or if the two adjacent angles read clockwise from the first-type notch 11 is a larger angle (e.g., $\theta_1$) followed by a smaller angle (e.g., $\theta_2$). Similar determinations may be made regarding the bottom surface of the microflake 100.

FIG. 2A shows that the first-type notch 21 may be formed by removing a non-isosceles triangular portion from a corner of the microflake 200 (shown in dotted lines). As shown in FIG. 2A and FIG. 2B, the first-type notch 21 forms an asymmetric relationship with its two adjacent sides (e.g., "a" and "d"), where a and d have different lengths (e.g., a>d). Alternatively or additionally, the first-type notch 21 may form an asymmetric relationship with its two adjacent angles (e.g., $\theta_1$ and $\theta_2$), where $\theta_1$ and $\theta_2$ have different values (e.g., $\theta_1 < \theta_2$). This difference in adjacent side lengths and/or adjacent angles helps a detector to determine whether an observed surface of a microflake is the top surface or the bottom surface of the microflake 200.

FIG. 3A shows that the first-type notch 31 may be formed by removing a wedge portion from the microflake 300 (shown in dotted lines). As shown in FIG. 3A and FIG. 3B, the first-type notch 31 forms an asymmetric relationship with its two adjacent angles (e.g., $\theta_1$ and $\theta_2$), where $\theta_1$ and $\theta_2$ have different values (e.g., $\theta_1 < \theta_2$). The first-type notch 31 may also form an asymmetric relationship with the two sides of the wedge portion that forms the first-type notch 31. This difference in adjacent angles and/or side lengths helps a detector to determine whether an observed surface of a microflake is the top surface or the bottom surface of the microflake 300.

FIGS. 4-7 illustrate a top view of encoded microflakes according to some embodiments. The code of a microflake is a binary sequence of ones and zeros, represented by the presence or absence of second-type notches at the edge of the microflake. To simplify the description, the following examples assume that the presence of a second-type notch indicates a binary "1" value and the absence of a second-type notch indicates a binary "0" value. An absent second-type notch is equivalent to an edge segment that is present at the same location. It is understood that the representation of "1" and "0" may be reversed in alternative embodiments. The second-type notches can be of any shape, as long as it is different from the shape of the first-type notch.

In one embodiment, a detector may read the code of a microflake as follows. Starting from the first-type notch, the detector may check the edge outline of the microflake at a fixed interval of physical distance (e.g., a unit length X) to identify whether a second-type notch is present or absent. The detector may start reading the code at a predetermined distance from one end of the first-type notch, in a predetermined direction (e.g., clockwise or counter-clockwise) based on whether the observed surface is the top surface or the bottom surface. For example, the code (from the least significant bit (LSB) to the most significant bit (MSB)) may be defined to be the bit sequence read clockwise from the top surface of the microflake. An alternative definition may also be used.

Figure 4:
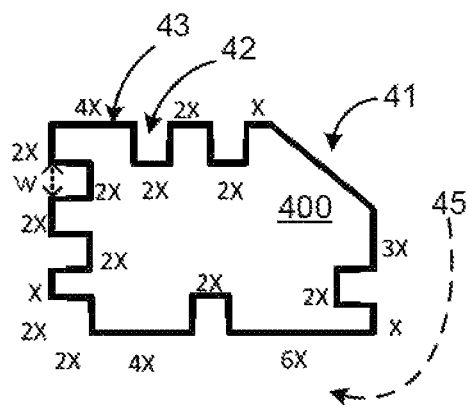
FIGS. 4, 5, 6 and 7 illustrate a top view of encoded microflakes according to some embodiments.

FIG. 4 illustrates a top view of an encoded microflake 400 according to one embodiment. In this example, the code from the LSB to the MSB is read clockwise in this top view from the first-type notch 41 in the direction of dotted arrow 45. The shape of each second-type notch in this example is defined by its two substantially parallel sides (only one of the second-type notches is labeled 42 to simplify the illustration) and a bottom side adjoining the two substantially parallel sides. The portion of the edge outline, where neither a first-type notch nor a second-type notch is present, is referred to as an edge segment (only one of the edge segments is labeled 43 to simplify the illustration). The top view of the microflake 400 shows an edge outline, which is a combination of edge segments, sides of the first-type notch and the second-type notches. In this example, each edge segment of length X is interpreted as a "0" bit and each second-type notch of length X is interpreted as a "1" bit. The length of a second-type notch may be defined as the length measured across the two sides of its opening indicated by "w" (only one is labeled to simplify the illustration). Two consecutive second-type notches may occupy a corner; e.g., the lower-left corner as shown in the top view. The edge outline of the microflake 400, represented by a sequence of lengths, in the order of being read (clockwise) is as follows: 3X→(2X)→X→6X→(2X)→4X→(2X)→(2X)→X→(2X)→2X→(2X)→2X→4X→(2X)→2X→(2 X)—>X, where the value in the parenthesis indicates the length of a corresponding second-type notch (i.e., representing one or more "1"s). Accordingly, the above sequence of lengths can be interpreted into the digital code (from LSB to MSB) identifying the microflake 400 as: 0110011000001100110111100001100000011000, which is read from right to left to correspond to the aforementioned clockwise order, and where LSB is the rightmost bit and MSB is the leftmost bit.

Figure 5:
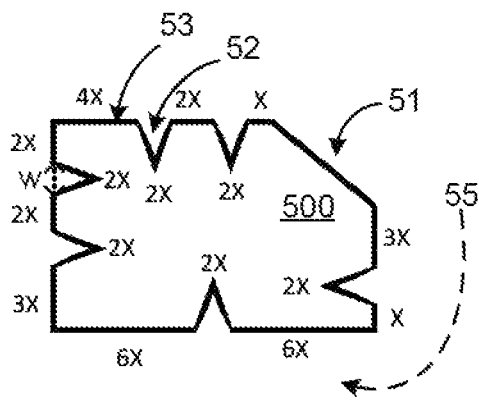

FIG. 5 illustrates a top view of an encoded microflake 500 according to another embodiment. In this example, the code from the LSB to the MSB is read clockwise in this top view from the first-type notch 51 in the direction of dotted arrow 55. Each second-type notch in this example is defined by two sides that join at one end (only one of the second-type notches is labeled 52 to simplify the illustration). From the top view, each second-type notch has a triangular shape. The edge outline of the microflake 500 can be read and interpreted into a digital code similarly to that of the microflake 400 in FIG. 4.

Figure 6:
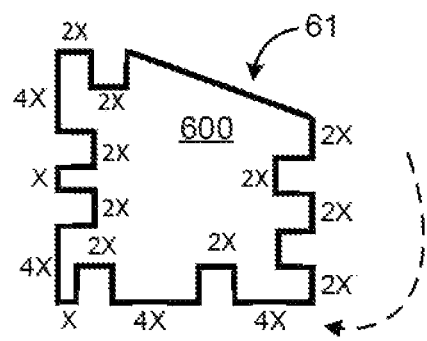
Figure 7:
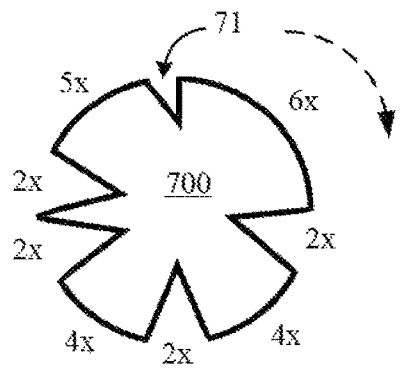

FIG. 6 and FIG. 7 illustrate a top view of an encoded microflake 600 and an encoded microflake 700, respectively, according to some other embodiments. The microflakes 600 and 700 have first-type notches 61 and 71, respectively. The codes associated with the microflakes 600 and 700 can be read and interpreted into respective digital codes according to the aforementioned description in connection with the microflakes 400 and 500.

The second-type notches shown in FIGS. 4-7 have symmetrical shapes. In alternative embodiments, a second-type notch may have an asymmetrical shape; e.g., one side is longer than the other side. A second-type notch can have any shape, as long as the shape is distinguishable from the shape of a first-type notch.

In one embodiment, the opening of a second-type notch can be of any length (measured across the two sides of its opening) that is an integer multiple of a predetermined unit length (e.g., denoted by X in FIGS. 4-7). In some embodiments, the length of a second-type notch's opening defines the number of consecutive bits having a first binary value in the binary sequence (i.e., the digital code), and the length of each edge segment defines the number of consecutive bits having a second binary value in the binary sequence. In some embodiments, the length of a second-type notch is limited to a predetermined length; e.g., one or two unit lengths. For example, a microflake may include a sequence of consecutive unit-length second-type notches to represent a long sequence of "1s".

Figure 8A:
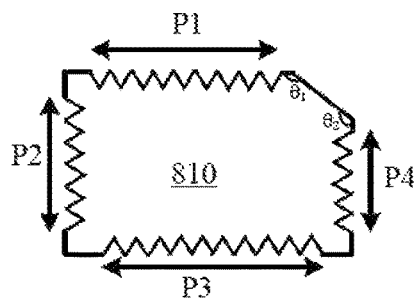
FIGS. 8A, 8B, 8C and 8D illustrate a top view of microflakes encoded with four different codes according to one embodiment.
Figure 8B:
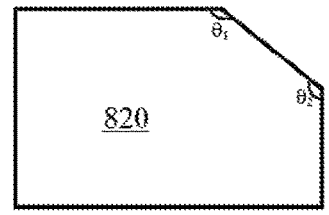

FIGS. 8A and 8B illustrate a top view of two encoded microflakes 810 and 820, respectively, according to some embodiments. Each of the microflakes 810 and 820 has a first-type notch at the upper-right corner in the top view. The microflake 810 is encoded with a sequence of ones using a sequence of consecutive unit-length second-type notches. In the example of FIG. 8A, the second-type notches are formed within predetermined portions of the edge outline (e.g., P1, P2, P3 and P4), avoiding the vicinity of the corner areas. One side of the second-type notch (representing the MSB or the LSB of the code) may adjoin a side of the first-type notch. The microflake 820, which is without any second-type notches, is encoded with a sequence of zeros.

Figure 8C:
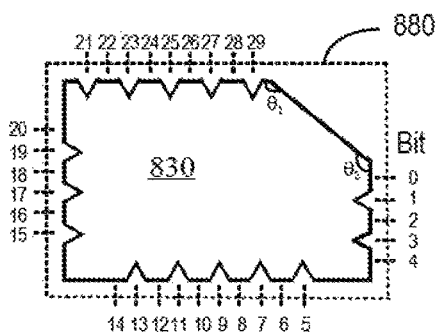
Figure 8D:
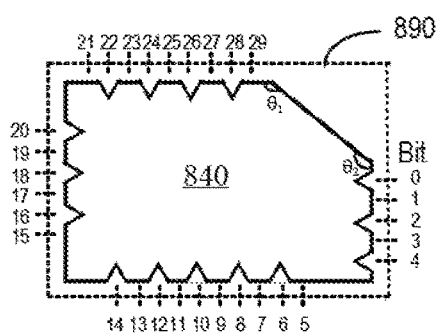

FIGS. 8C and 8D illustrate the top view of two encoded microflakes 830 and 840, respectively, according to some embodiments. Each of the microflakes 830 and 840 has a first-type notch at the upper-right corner in the top view. Each of the microflakes 830 and 840 is encoded with a sequence of alternating ones and zeros using a sequence of second-type notches and edge segments. In these examples, the codes (from the LSB to the MSB) associated with the microflakes 830 and 840, as shown in FIGS. 8C and 8D, are read and interpreted clockwise from the respective first-type notches.

FIGS. 8C and 8D further illustrate predefined locations surrounding the edge outline of the microflakes 830 and 840. The predefined locations of bits 0-29 of the code are marked on the dotted lines. In these embodiments, a bit has a first value if its predefined location has no second-type notch, and a bit has a second value if its predefined location has a second-type notch present. The spacing between adjacent predefined locations may be any value, as a detector does not measure the spacing in determining the bit values of a code. When reading the code, a detector may be provided with a detection template with marking of these predefined locations. The detection template may be overlaid on the image of a microflake's edge outline for the detector to determine whether a second-type notch is present at these locations. A detection template may have the same shape as the base shape of the microflake, with location markings for the bits. Examples of the detection templates may be the dotted rectangles 880 and 890 with the location markings in FIGS. 8C and 8D. A detection template may be larger, smaller or of the same size as the base shape of the microflake, as long as its location markings indicate the bit locations.

Figure 9A:
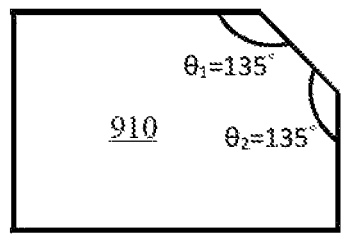
FIGS. 9A, 9B and 9C illustrate microflakes, each of which uses adjacent angles to encode a group identifier according to some embodiments.
Figure 9B:
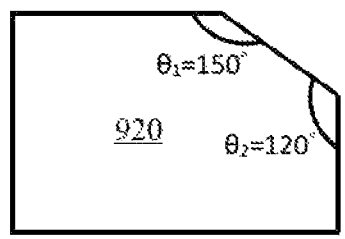
Figure 9C:
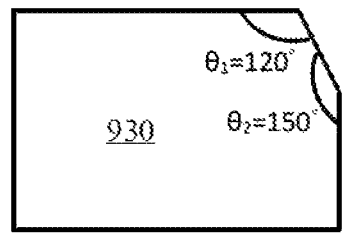

In one embodiment, a microflake may be identified by a group identifier in addition to a binary sequence formed by its edge segments and second-type notches. The group identifier may be encoded by a combination of the adjacent angles of the first-type notch, such as $\theta_1$ and $\theta_2$ shown in FIGS. 8A-8D. For ease of illustration, FIGS. 9A, 9B and 9C illustrate examples of three groups without any second-type notches. It is understood that the group identifiers can be combined with any of the binary sequences described herein to form a digital code of a microflake.

FIG. 9A illustrates a first example of a group identifier in which the two adjacent angles have the same value (e.g., $\theta_1=\theta_2=135°$). This is applicable to a microflake which has asymmetrical sides (e.g., a rectangle). FIG. 9B illustrates a second example of a group identifier, e.g., $\theta_1=150°$, $\theta_2=120°$. FIG. 9C illustrates a third example of a group identifier, e.g., $\theta_1=120°$, $\theta_2=150°$. In one embodiment, different values of angle_diff=$(\theta_1-\theta_2)$ correspond to different group identifiers. In one embodiment, the value of angle_diff may be represented by a number of bits, where the number is determined according to the number of groups.

Figure 10A:
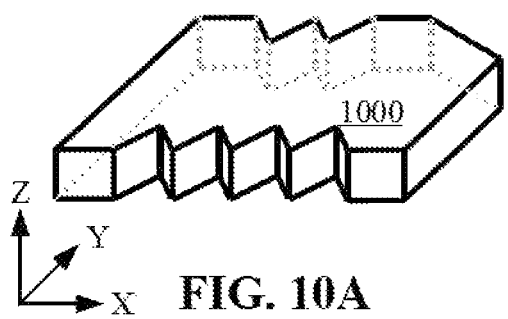
FIGS. 10A and 10B illustrate a three-dimensional view and a cross-section view, respectively, of a digitally encoded magnetic microflake according to one embodiment.
Figure 10B:
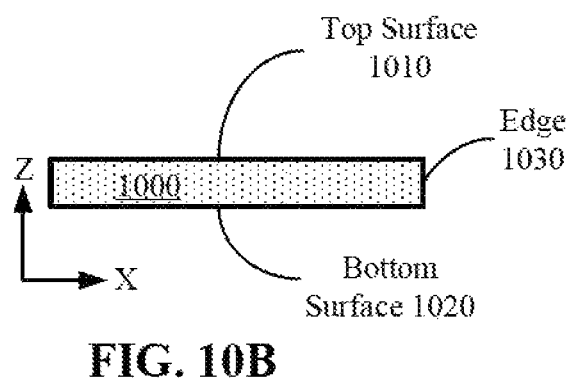

FIGS. 10A and 10B illustrate a three-dimensional (3D) view and a cross-sectional view of a microflake 1000, respectively, according to one embodiment. The cross-sectional view of the microflake 1000 in FIG. 10B shows a top surface 1010, a bottom surface 1020 substantially parallel to the top surface 1010, and an edge 1030 (i.e., the periphery) surrounding the top surface 1010 and the bottom surface 1020. The top surface 1010 and the bottom surface 1020 are substantially planar; e.g., substantially parallel to the horizontal plane spanned by the X-Y axes (i.e., the X-Y plane) as shown. The edge 1030 is substantially perpendicular to the two surfaces 1010 and 1020; e.g., substantially parallel to the Z-axis as shown. As shown in FIG. 10B, the edge 1030 extends vertically between the top surface 1010 and the bottom surface 1020. In one embodiment, the top surface 1010 and the bottom surface 1020 may be symmetric with respect to the X-Y plane. When used in a multiplex assay, either one or both of the surfaces 1010 and 1020 may be coupled to reagents (e.g., probes) for bonding with target analytes.

In one embodiment, the microflake 1000 is made of a magnetic polymer material, which is substantially transparent. The magnetic polymer material may be produced by mixing magnetic metal particles into the polymer. The microflake 1000, which is magnetically responsive, can be easily manipulated and handled with magnetic fields during the process of a multiplex assay.

Figure 10C:
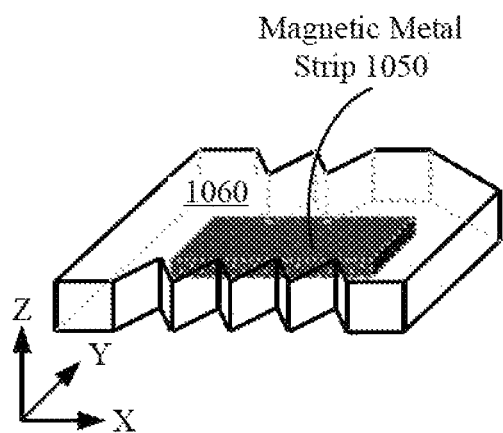
FIGS. 10C and 10D illustrate a three-dimensional view and a cross-section view, respectively, of a digitally encoded magnetic microflake according to another embodiment.

FIG. 10C illustrates an edge outline 1080 of the microflake 1000 according to one embodiment. The edge outline 1080 encodes the microflake 1000 according to any one of the aforementioned edge encoding schemes. FIG. 10C shows that the edge outline 1080 outlines the periphery of both the top surface 1010 and the bottom surface 1020 on a plane (e.g., the X-Y plane in this example). The plane is substantially parallel to the top surface 1010 and the bottom surface 1020. Thus, a detector can detect the same code of the microflake 1000 from both surfaces 1010 and 1020. The same binary sequence of the code may be read clockwise from one of the surfaces 1010 and 1020, and counter-clockwise from the other one of the surfaces 1010 and 1020.

Figure 10D:
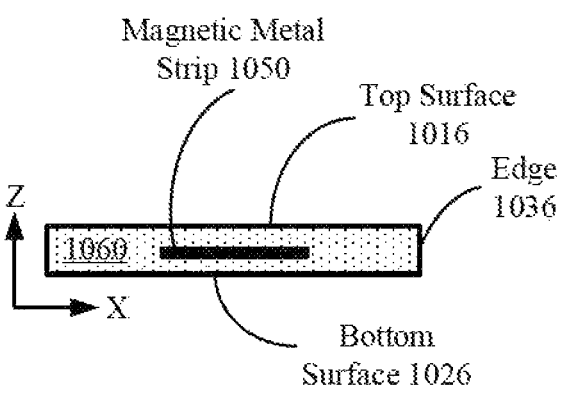

FIGS. 10C and 10D illustrate a 3D view and a cross-sectional view of a microflake 1060, respectively, according to another embodiment. Similar to the microflake 1000 in FIGS. 10A and 10B, the microflake 1060 also includes a top surface 1016, a bottom surface 1026 substantially parallel to the top surface 1016, and an edge 1036 surrounding the top surface 1016 and the bottom surface 1026. In addition, the microflake 1060 has a magnetic metal strip 1050, e.g., nickel, cobalt, iron, or the like, embedded therein. The magnetic metal strip 1050 is a non-transparent (i.e., opaque) layer embedded within the microflake 1060. The magnetic metal strip 1050 may be sandwiched between a top transparent polymer layer and a bottom transparent polymer layer of the microflake 1060. In one embodiment, the magnetic metal strip 1050 is located at a geometric center of the microflake 1060. The geometric center location helps to reduce the torque on the microflake 1060 when the microflake 1060 is picked up or collected with a magnetic field during a multiplex assay process. Similar to the microflake 1000 in FIG. 10A, the microflake 1060 is encoded by its edge outline which outlines the periphery of both the top surface 1016 and the bottom surface 1026 on a plane substantially parallel to the top surface 1016 and the bottom surface 1026.

Figure 10E:
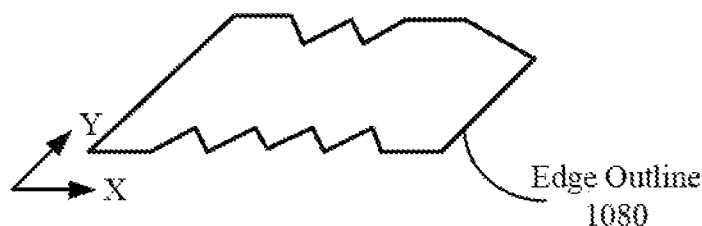
FIG. 10E illustrates an edge outline of a microflake according to one embodiment.
Figure 11A:
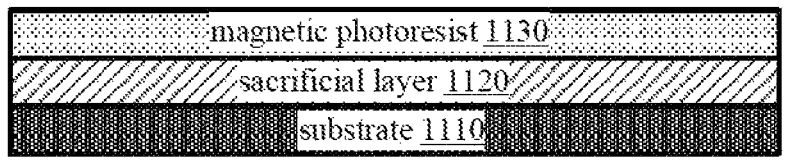
FIGS. 11A, 11B, 11C and 11D illustrate steps of fabricating microflakes according to a first embodiment.
Figure 11B:
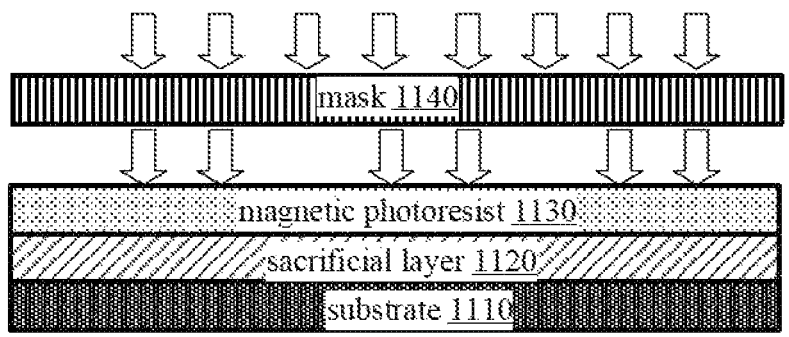
Figure 11C:
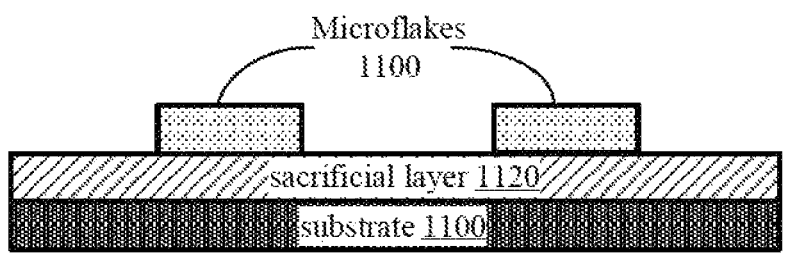
Figure 11D:
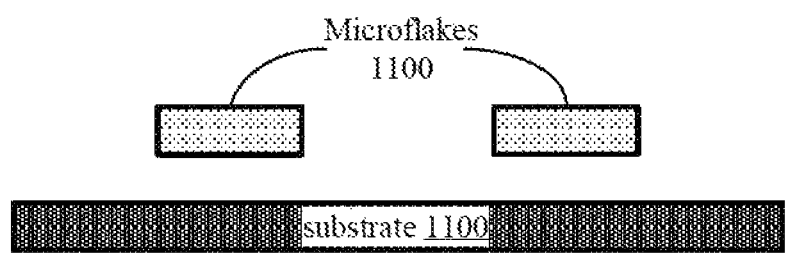

FIG. 10E illustrates an edge outline 1080 of the microflake 1000 or 1060 according to one embodiment. The edge outline 1080 encodes the microflake 1000 according to any one of the aforementioned edge encoding schemes. Using the microflake 1000 as an example, FIG. 10E shows that the edge outline 1080 outlines the periphery (i.e., edge) of both the top surface 1010 and the bottom surface 1020 on a plane (e.g., the X-Y plane in this example). The plane is substantially parallel to the top surface 1010 and the bottom surface 1020. Thus, a detector can detect the same code of the microflake 1000 from either one of the surfaces 1010 and 1020. The same binary sequence of the code may be read clockwise from one of the surfaces 1010 and 1020, and counter-clockwise from the other one of the surfaces 1010 and 1020.

The aforementioned microflakes may be fabricated based on techniques developed for semiconductor fabrication and/or micro-electro-mechanical systems (MEMS) fabrication. For example, the microflake fabrication described below uses substrate materials, sacrificial materials, and photoresist materials that are known in the art of the semiconductor and/or MEMS fabrication. A number of steps known to skilled persons in the field of semiconductor and/or MEMS fabrication are omitted below to simplify the illustration. For example, omitted steps may include surface cleaning to prepare surfaces for subsequent processing, soft-baking to remove solvents, etc. The fabrication processes described below are simpler, cost less and reserve more reaction areas compared with a process for fabricating conventional microcarriers.

Figure 14:
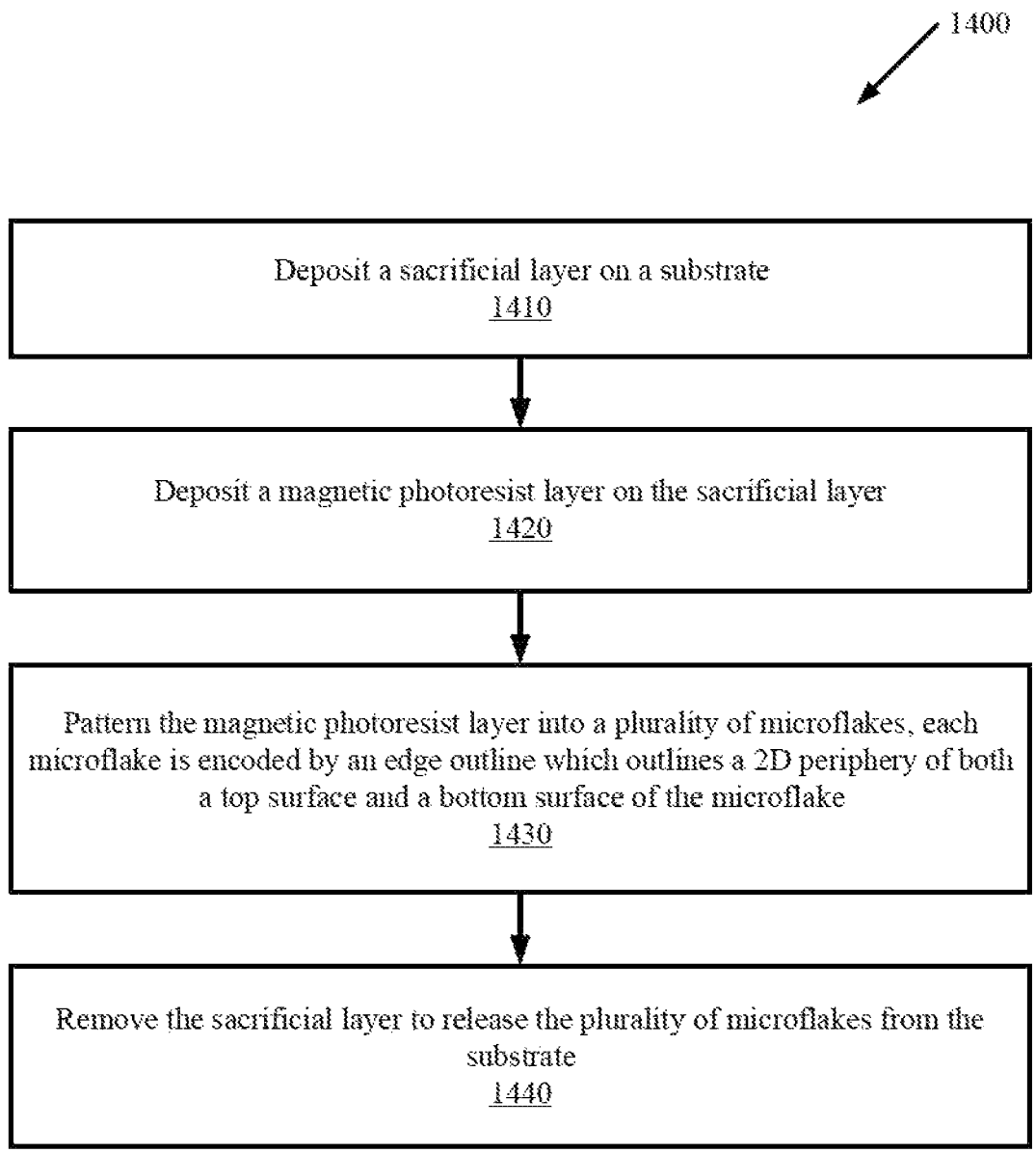
FIG. 14 is a flow diagram illustrating a method for fabricating digitally encoded magnetic microflakes according to a first embodiment.

FIGS. 11A, 11B, 11C and 11D illustrate steps of fabricating microflakes according to a first embodiment. FIG. 14 is a flow diagram illustrating a method 1400 for fabricating microflakes according to the first embodiment. Examples of the microflakes fabricated according to the first embodiment include, but are not limited to, the microflake 1000 of FIGS. 10A and 10B. Referring to FIGS. 11A-11D and 14, the method 1400 starts at step 1410 with depositing a sacrificial layer 1120 on top of a substantially planar substrate 1110 on a wafer. Subsequently at step 1420, a magnetic photoresist layer 1130 (e.g., a magnetic polymer layer) is deposited on top of the sacrificial layer 1120. The magnetic photoresist layer 1130 may be substantially transparent or at least partially transparent in some embodiments. A mask layer 1140 which contains microflake patterns is used, at step 1430, to pattern the magnetic photoresist layer 1130 into microflakes. The mask layer 1140 selectively exposes areas of the magnetic photoresist layer 1130 to ultraviolet (UV) light to thereby define the individual microflakes 1100. Each microflake 1100 is encoded by its edge outline which outlines a 2D periphery of both the top surface and the bottom surface of the microflake 1100 on a plane that is substantially parallel to the top and bottom surfaces. In one embodiment, the mask layer 1140 may define microflakes encoded with different codes on the wafer. Thus, microflakes with different codes may be fabricated at the same time on the same wafer. At step 1440, the sacrificial layer 1120 is etched or otherwise removed to release the microflakes 1100 from the substrate 1110.

Figure 12A:
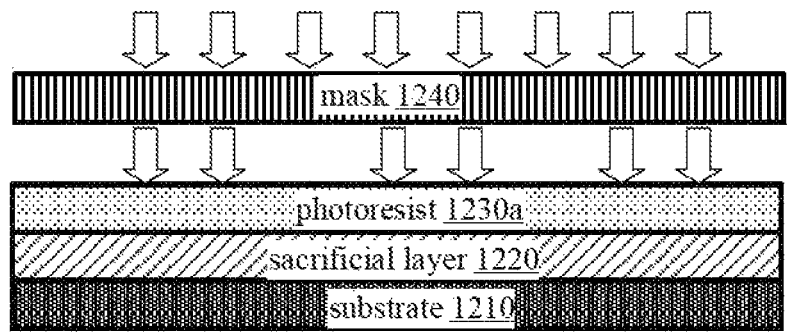
FIGS. 12A, 12B, 12C, 12D, 12E, 12F, 12G, 12H and 12I illustrate steps of fabricating microflakes according to a second embodiment.
Figure 12B:
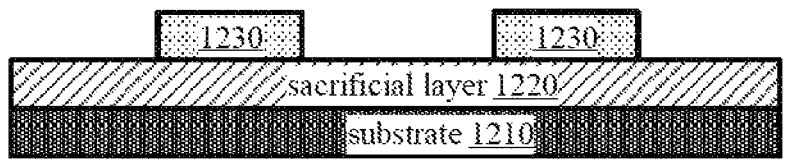
Figure 12C:
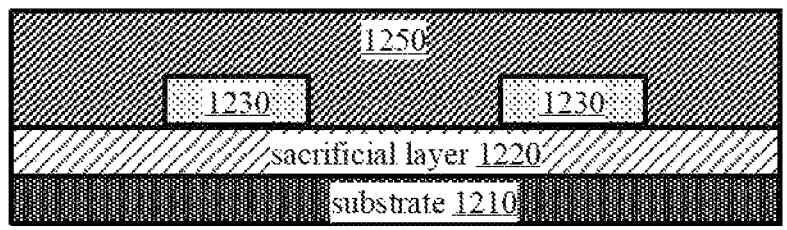
Figure 12D:
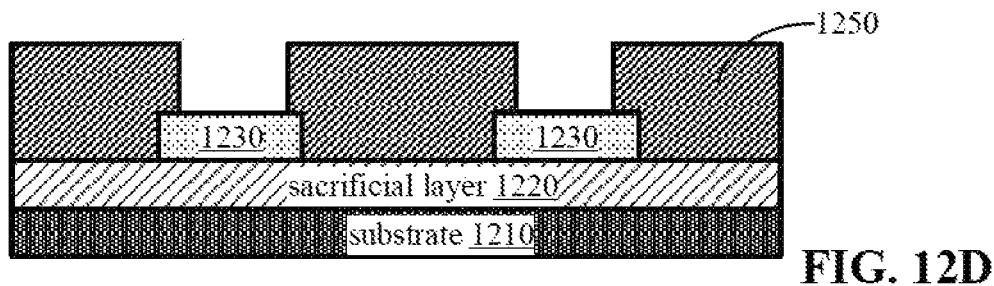
Figure 12E:
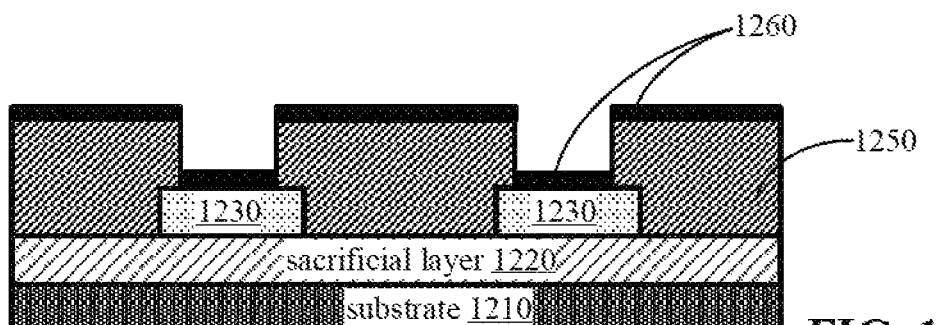
Figure 12F:
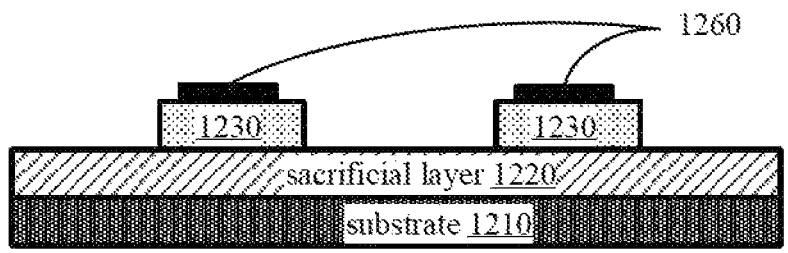
Figure 12G:
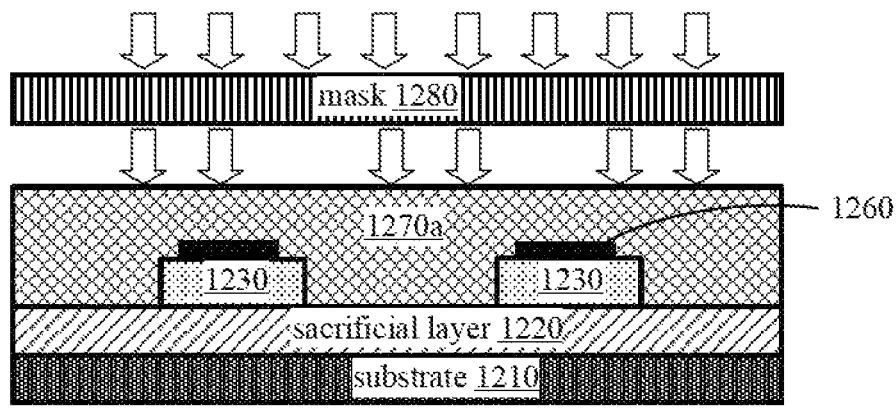
Figure 12H:
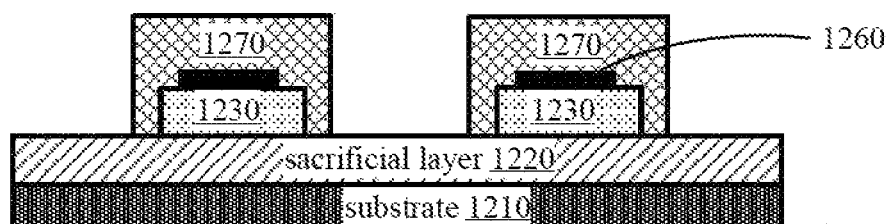
Figure 12I:
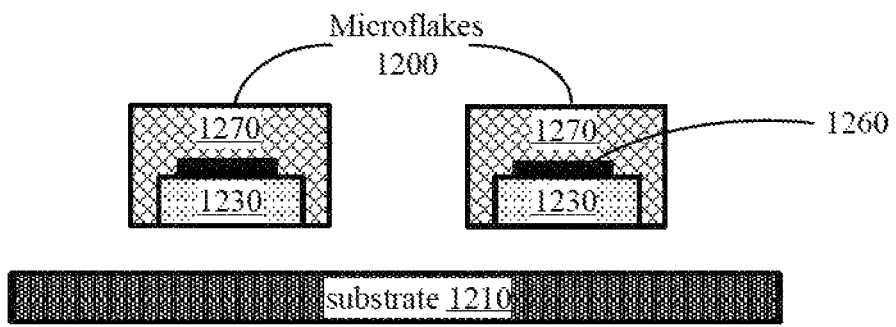
Figure 15:
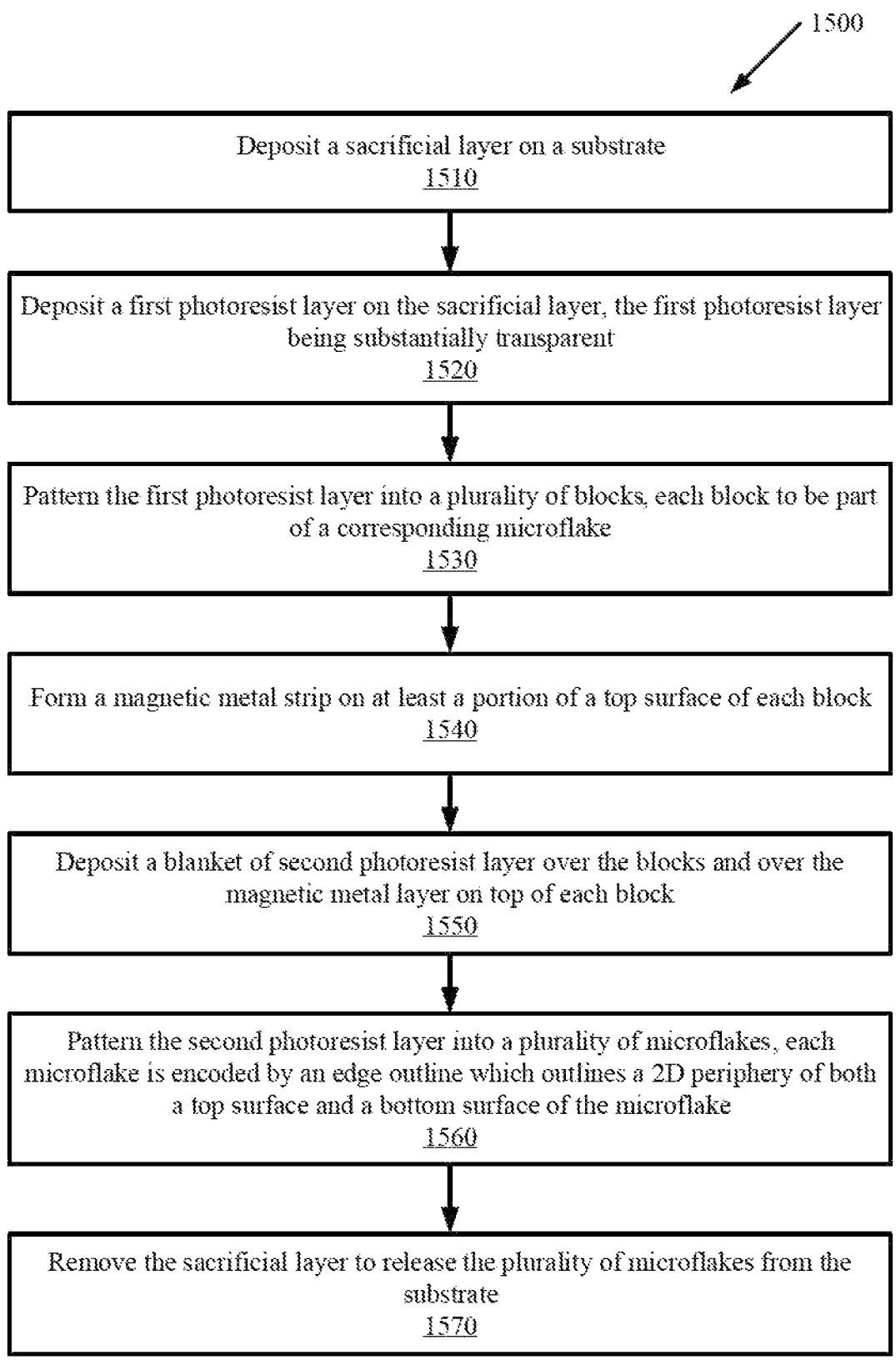
FIG. 15 is a flow diagram illustrating a method for fabricating digitally encoded magnetic microflakes according to a second embodiment.

FIGS. 12A-12I illustrate steps of fabricating microflakes according to a second embodiment. FIG. 15 is a flow diagram illustrating a method 1500 for fabricating microflakes according to the second embodiment. Examples of the microflakes fabricated according to the second embodiment include, but are not limited to, the microflake 1060 of FIGS. 10C and 10D. Referring to FIGS. 12A, 12B and 15, the method 1500 starts at step 1510 with depositing a sacrificial layer 1220 on top of a substantially planar substrate 1210 on a wafer. Subsequently at step 1520, a photoresist layer 1230a (e.g., a polymer layer) is deposited on top of the sacrificial layer 1220. The photoresist layer 1230a may be substantially transparent or at least partially transparent in some embodiments. A mask layer 1240 which contains microflake patterns is used, at step 1530, to pattern the photoresist layer 1230a into multiple blocks 1230, where each block 1230 is to be part of a corresponding microflake. The mask layer 1240 selectively exposes areas of the photoresist layer 1230 to UV light to thereby define the individual blocks 1230.

A lift-off process may be performed to deposit a magnetic metal layer on each bottom portion. FIGS. 12C-12F illustrate the lift-off process according to one embodiment. A second sacrificial material 1250 is blanket-deposited on top of the remaining structure. The second sacrificial material 1250 is patterned to expose at least a portion of the top surface of each block 1230. A thin layer of a magnetic metal 1260 is deposited to cover the entire top of the patterned sacrificial material 1250 and the exposed blocks 1230, by Physical Vapor Deposition (PVD), Chemical Vapor Deposition (CVD), etc. The second sacrificial material 1250 is then stripped off, e.g., by using a chemical solution or alternative means. Thus, at step 1540, a strip of the magnetic metal layer 1260 is formed on at least a portion of the top surface of each block 1230.

Referring to FIGS. 12G-12I and 15, at step 1550, another photoresist layer 1270a (e.g., a polymer layer) is blanket-deposited over the remaining structure; i.e., over the blocks 1230 and over the magnetic metal layer 1260 on top of each block 1230. In one embodiment, the photoresist layer 1270a may be the same material as the photoresist layer 1230a. The photoresist layer 1270a may be substantially transparent or at least partially transparent in some embodiments. At step 1560, a mask layer 1280 which contains microflake patterns is used to pattern the photoresist layer 1270a into microflakes 1200. Each microflake 1200 is encoded by its edge outline which outlines a 2D periphery of both the top surface and the bottom surface of the microflake 1200 on a plane that is substantially parallel to the top and bottom surfaces. In one embodiment, the mask layer 1280 may define microflakes encoded with different codes on the wafer. Thus, microflakes with different codes may be fabricated at the same time on the same wafer. At step 1570, the sacrificial layer 1220 is etched or otherwise removed to release the microflakes 1200 from the substrate 1210.

Figure 13:
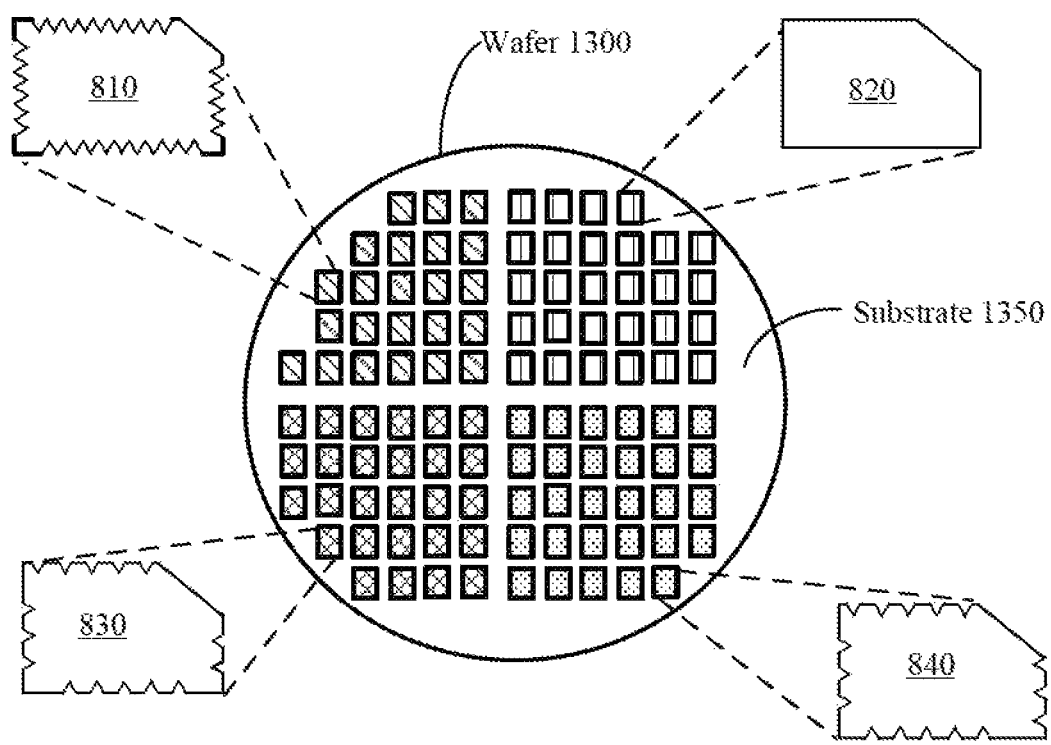
FIG. 13 is a schematic diagram illustrating a semiconductor wafer including microflakes encoded with different codes according to one embodiment.

FIG. 13 is a schematic diagram illustrating a semiconductor wafer 1300 having a plurality of microflakes on a substrate 1350 according to one embodiment. The example of FIG. 13 shows that microflakes with different codes can be fabricated on the same wafer; e.g., by patterning the microflakes with a mask layer that defines different edge outlines corresponding to the different codes. Non-limiting examples of the patterning step have been provided at step 1430 in FIG. 14 and step 1560 in FIG. 15. For example, the wafer 1300 may be fabricated to include the microflakes 810, 820, 830 and 840 (FIGS. 8A-8D). In one embodiment, the wafer 1300 may include multiple partitions, with each partition including a group of microflakes of the same code. It is understood that in alternative embodiments, a wafer may include microflakes having more different codes, or fewer different codes, than what is shown in FIG. 13.

The aforementioned microflakes may have a number of uses, including but not limited to, a multiplex assay kit. The multiplex assay kit includes at least a first microflake according to any of the above embodiments to form a target-specific bonding to a first target analyte, and a second microflake according to any of the above embodiments to form a target-specific bonding to a second target analyte which is different from the first target analyte. The first microflake is identified by a first binary sequence, and the second microflake is identified by a second binary sequence. The first binary sequence is encoded by a first edge outline, which outlines a periphery of the first microflake on a first plane substantially parallel to a top surface and a bottom surface of the first microflake. The second binary sequence is encoded by a second edge outline, which outlines a periphery of the second microflake on a second plane substantially parallel to a top surface and a bottom surface of the second microflake.

Figure 16:
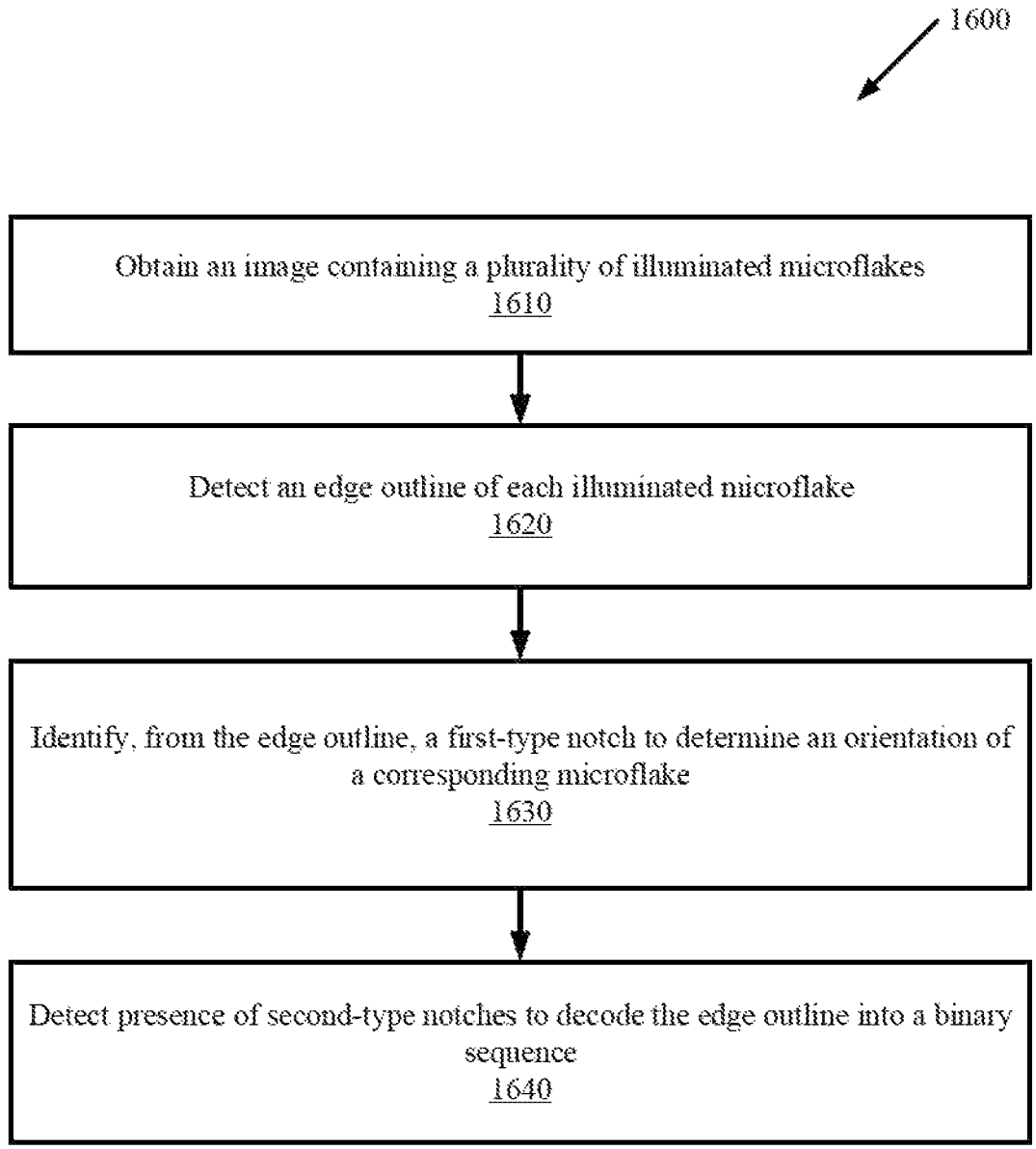
FIG. 16 is a flow diagram illustrating a method for decoding digitally encoded magnetic microflakes according to one embodiment.

FIG. 16 is a flow diagram illustrating a method 1600 for decoding digitally encoded magnetic microflakes according to one embodiment. The method 1600 may be performed by a detector, such as a machine to be described in connection with FIG. 17. The method 1600 begins at step 1610 where the detector obtains an image containing a plurality of illuminated microflakes. At step 1620, the detector detects an edge outline of each illuminated microflake. From the edge outline, the detector at step 1630 identifies a first-type notch to determine an orientation of a corresponding microflake. At step 1630, the detector detects the presence (or absence) of second-type notches to decode the edge outline into a binary sequence. The binary sequence is the digital code identifying the corresponding microflake.

Figure 17:
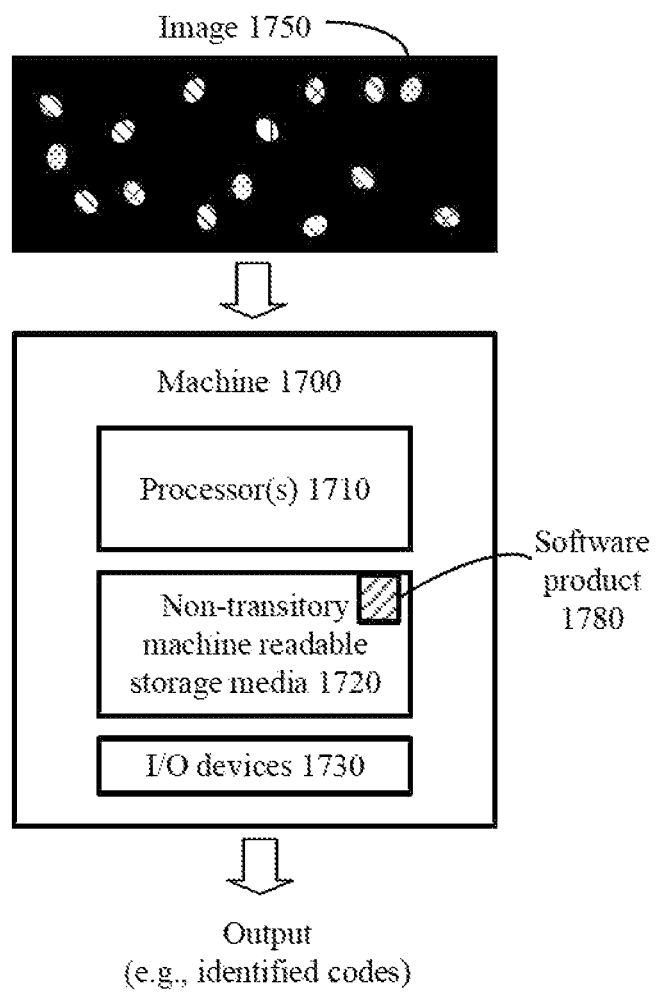
FIG. 17 is a diagram illustrating a machine operable to execute a software product for decoding encoded microflakes according to one embodiment.

FIG. 17 is a diagram illustrating a machine 1700 operable to execute a software product 1780 for decoding the encoded microflakes according to one embodiment. The software product 1780 may be stored in a machine-readable medium (such as the non-transitory machine-readable storage media 1720, also referred to as a computer-readable medium, a processor-readable medium, or a computer-usable medium having a computer-readable program code embodied therein). The non-transitory machine-readable medium 1720 may be any suitable tangible medium including a magnetic, optical, or electrical storage medium including a diskette, compact disk read-only memory (CD-ROM), digital versatile disc read-only memory (DVD-ROM) memory device (volatile or non-volatile) such as hard drive or solid-state drive, or another storage mechanism. The machine-readable medium 1720 may contain various sets of instructions, code sequences, configuration information, or other data, which, when executed, cause a processor 1710 to decode the encoded microflakes in an image 1750; e.g., according to the method 16 of FIG. 16. The image 1750 may be obtained by an I/O device 1730 of the machine 1700. From the image 1750, the machine 1710 may generate an output that includes at least the identified codes associated with the microflakes. Those of ordinary skill in the art will appreciate that other instructions and operations necessary to implement the described embodiments may also be stored on the machine-readable medium 1720. Software running from the machine-readable medium may interface with circuitry to perform the described tasks.

While the invention has been described in terms of several embodiments, those skilled in the art will recognize that the invention is not limited to the embodiments described, and can be practiced with modification and alteration within the spirit and scope of the appended claims. The description is thus to be regarded as illustrative instead of limiting.

What is claimed is:

1. An apparatus for a multiplex assay, comprising:
a first microflake to form a target-specific bonding to a first target analyte; and
a second microflake to form a target-specific bonding to a second target analyte which is different from the first target analyte,
wherein the first microflake is identified by a first binary sequence, and the second microflake is identified by a second binary sequence different from the first binary sequence,
the first binary sequence is encoded by a first edge outline on a first plane substantially parallel to a top surface and a bottom surface of the first microflake, and bits in the first binary sequence are encoded at respective predefined locations surrounding the first edge outline,
the second binary sequence is encoded by a second edge outline on a second plane substantially parallel to a top surface and a bottom surface of the second microflake, and bits in the second binary sequence are encoded at respective predefined locations surrounding the second edge outline,
each of the first edge outline and the second edge outline includes a first-type notch which indicates a starting point and a direction along which the first binary sequence or the second binary sequence is to be read, and
each of the first microflake and the second microflake is further identified by a group identifier which is encoded by adjacent angles of the first-type notch, and wherein different combinations of the adjacent angles encode different group identifiers.

2. The apparatus of claim 1, wherein each of the first microflake and the second microflake includes a substantially transparent polymer layer.

3. The apparatus of claim 2, wherein the substantially transparent polymer layer is a magnetic polymer layer.

4. The apparatus of claim 2, wherein a magnetic metal strip is embedded within and located at a geometric center of the substantially transparent polymer layer.

5. The apparatus of claim 1, wherein each of the first edge outline and the second edge outline includes the first-type notch which further functions as an orientation indicator, and at least one of the first edge outline and the second edge outline includes a second-type notch representing a binary value in the first binary sequence or the second binary sequence.

6. The apparatus of claim 1, wherein presence of a second-type notch at a predefined location of each of the first edge outline and the second edge outline corresponds to a first binary value, and absence of the second-type notch at the predefined location of each of the first edge outline and the second edge outline corresponds to a second binary value.

7. An apparatus of a semiconductor wafer, comprising:
a substrate;
a plurality of first microflakes on the substrate, each first microflake identified by a first binary sequence; and
a plurality of second microflakes on the substrate, each second microflake identified by a second binary sequence different from the first binary sequence,
wherein the first binary sequence encoded by a first edge outline on a plane substantially parallel to the substrate, and bits in the first binary sequence are encoded at respective predefined locations surrounding the first edge outline,
the second binary sequence encoded by a second edge outline on the plane, and bits in the second binary sequence are encoded at respective predefined locations surrounding the second edge outline,
each of the first edge outline and the second edge outline includes a first-type notch which indicates a starting point and a direction along which the first binary sequence or the second binary sequence is to be read, and
each of the first microflake and the second microflake is further identified by a group identifier which is encoded by adjacent angles of the first-type notch, and wherein different combinations of the adjacent angles encode different group identifiers.

8. The apparatus of claim 7, wherein each microflake of the first microflakes and the second microflakes includes a substantially transparent polymer layer.

9. The apparatus of claim 8, wherein a magnetic metal strip is embedded within and located at a geometric center of the substantially transparent polymer layer.

10. The apparatus of claim 7, wherein each microflake of the first microflakes and the second microflakes is magnetic.

11. The apparatus of claim 7, wherein each of the first edge outline and the second edge outline includes the first-type notch which further functions as an orientation indicator, and wherein at least one of the first edge outline and the second edge outline includes a second-type notch representing a binary value in the first binary sequence or the second binary sequence.

12. The apparatus of claim 7, wherein presence of a second-type notch at a predefined location of each of the first edge outline and the second edge outline corresponds to a first binary value, and absence of the second-type notch at the predefined location of each of the first edge outline and the second edge outline corresponds to a second binary value.

* * * * *